United States Patent
Tsai

(10) Patent No.: US 6,994,870 B2
(45) Date of Patent: Feb. 7, 2006

(54) LOCAL NASAL IMMUNOTHERAPY WITH ALLERGEN STRIP FOR ALLERGIC RHINITIS

(76) Inventor: Jaw-Ji Tsai, 3Fl.-2, No. 499, Lane 150, Sec. 5, Shinyi Rd., Shinyi Chiu, Taipei (TW)

( * ) Notice: Subject to any disclaimer, the term of this patent is extended or adjusted under 35 U.S.C. 154(b) by 229 days.

(21) Appl. No.: 10/325,921

(22) Filed: Dec. 23, 2002

(65) Prior Publication Data

US 2004/0052808 A1    Mar. 18, 2004

Related U.S. Application Data

(63) Continuation-in-part of application No. 10/245,514, filed on Sep. 18, 2002.

(51) Int. Cl.
*A61K 9/70* (2006.01)
*A61K 39/35* (2006.01)

(52) U.S. Cl. .................. 424/443; 424/447; 424/275.1; 424/449; 424/184.1; 514/44; 514/826

(58) Field of Classification Search ............... 424/443, 424/447, 275.1, 449, 184.1; 514/44, 826
See application file for complete search history.

(56) References Cited

U.S. PATENT DOCUMENTS

2003/0078223 A1 *  4/2003  Raz et al. ..................... 514/44
2003/0104013 A1 *  6/2003  Loria et al. .............. 424/275.1
2004/0047902 A1 *  3/2004  Dupont et al. .............. 424/449

OTHER PUBLICATIONS

Adrienne Verhoef et al., "Threshold Signaling of Human Th0 Cells in Activation and Anergy: Modulation of Effector Function by Altered TCR Ligand", The Journal of Immunology, pp. 6034-6040 (2000).
Ko et al., "A New Fungal Immunomodulatory Protein, FIP-fveU Isolated From the Edible Mushroom, Flammulina Velutipes and Its Complex Amino Acid Sequence", Eur. J. Biochem, pp. 244-249 (1995).

* cited by examiner

*Primary Examiner*—Gary Kunz
*Assistant Examiner*—Mina Haghighatian
(74) *Attorney, Agent, or Firm*—Birch, Stewart, Kolasch & Birch, LLP

(57) ABSTRACT

A method and strip for treating allergen-induced airway inflammation. The method includes applying a nasal or skin strip containing a mixture of an allergen and a pharmaceutically acceptable carrier to an individual having allergen-induced airway inflammation in a manner consistent with local nasal immunotherapy.

10 Claims, 1 Drawing Sheet

1

LOCAL NASAL IMMUNOTHERAPY WITH ALLERGEN STRIP FOR ALLERGIC RHINITIS

This application is a CIP of patent application Ser. No. 10/245,514, filed Sep. 18, 2002.

BACKGROUND OF THE INVENTION

1. Field of the Invention

The present invention relates to local nasal immunotherapy for allergen-induced airway inflammation. More particularly, the present invention relates to an allergen strip for local nasal immunotherapy of allergic rhinitis.

2. Description of the Related Arts

Allergic Rhinitis (AR) is one of the most common allergic diseases in humans. In developed countries, more than 10% of the population suffer from AR and the disease creates burdens such as medical expenses and loss of productivity (Malone D C, et al. J Allergy Clin Immunol. (1997) 99:22–7). Allergen specific immunotherapy was introduced to treat AR by Noon in 1911 (Noon L. Lancet (1911) i:1572–3). There is good evidence that immunotherapy using inhalant allergens to treat seasonal or perennial AR and asthma is clinically effective (Bousquent J, et al. Allergy (1998) 53, suppl 54). Despite the effectiveness of subcutaneous immunotherapy, poor compliance and systemic side-effects may limit its applicability (Cohn J R, et al. J Allergy Clin Immunol. (1993) 91:734–7; Committee on the Safety of Medicine. CSM update. Desensitizing vaccines. BMJ (1986) 293:948; Greenberg M A, et al. J Allergy Clin Immunol. (1986) 77:865–70; Lockey R F, et al. J Allergy Clin Immunol (1987) 79:660–77). The reports of severe reactions questioned the safety of subcutaneous immunotherapy and raised an interest in local nasal immunotherapy (LNIT).

The clinical efficacy of LNIT has been documented in most double-blind, placebo-controlled studies carried out in AR (Georgitis J W, et al. J Allergy Clin Immunol (1983) 71:71–6; Georgitis J W, et al. J Allergy Clin Immunol (1984) 74:694–700; Andri L, et al. J Allergy Clin Immunol (1993) 91:987–96; Passalacqua G, et al. Am J Respir Crit Care Med (1995) 152:461–6; D'Amato G, et al. Clin Exp Allergy (1995) 25:141–8; Andri L, et al. Clin Exp Allergy (1995) 25:1092–9; Andri L, et al. J Allergy Clin-Immunol (1996) 97:34–41; Cirla A M, et al. Allergy (1996) 51:299–305; Bargare M, et al. J Investing Allergol Immunol (1996) 6:359–63). The allergens used for LNIT were dispensed in either powder form or an aqueous solution and tended to be inhaled into the lower airway easily. During the application of the allergens, the patient must vocalize to avoid deposition of extract in the bronchial tree. LNIT may induce asthmatic symptoms; thus, in one study, three patients in the active group withdrew from treatment because of bronchospasm after allergen application (D'Amato G, et al. Clin Exp Allergy (1995) 25:141–8). Critics of LNIT have also claimed that the treatment induces local symptoms for a prolonged period of time, however, the symptoms induced by LNIT were relatively mild.

SUMMARY OF THE INVENTION

It is therefore a primary object of the present invention to provide a safe and effective method for treating allergen-induced airway inflammation. The method comprises applying a nasal or skin strip containing a mixture of an allergen and a pharmaceutically acceptable carrier to an individual having allergen-induced airway inflammation in a manner consistent with local immunotherapy.

Another object of the present invention is to provide a nasal or skin strip for treating allergen-induced airway inflammation in an individual. The nasal or skin strip comprises a substrate, and a mixture of an allergen and a pharmaceutically acceptable carrier on the substrate.

In one embodiment, the allergen-induced airway inflammation comprises, but is not limited to, allergic rhinitis, allergic conjunctivitis, or allergic bronchial asthma. The allergen comprises, but is not limited to, dust mite extract, such as *Dermatophoides pteronyssinus* (Dp) extract, pollen extract, such as ragweed, mold extract, animal dander, cockroach extract, food allergen, recombinant allergen peptide, or a combination thereof. The skin or nasal strip further comprises an immunmodulatory adjuvant. The immunomodulatory adjuvant includes, but is not limited to, fungal immunomodulatory protein (FIP) isolated from *Flammalina velutipes,* immunostimulatory sequence CpG (CpG oligodeoxynucleotides) or mycobacterium-Bacillus Calmette Guerin (BCG).

In a second embodiment, the allergen is in a dosage of 0.01~10 µg, preferably 0.01~1 µg. The FIP is in a dosage of 0.01~10 µg, preferably 0.5 µg.

In another embodiment, the substrates of the nasal or skin strip include nitrocellulose (NC), polyvinylidene fluoride (PVDF), nylon, filter papers, fabric, cloth, polyethylene, polypropylene, composite fibers, flexible medical grade materials, or a combination thereof. The pharmaceutically acceptable carrier includes, but is not limited to, detergent, lipid solvent, glycerol, PBS, normal saline, water, petrolatum, or vaseline. The detergent includes lecithin or alpha hydroxyl acid, and the lipid solvent includes alcohol or mint.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be more fully understood from the detailed description given hereinbelow and the accompanying drawings, which are given by way of illustration only, and thus are not limitative of the present invention, and in which.

DETAILED DESCRIPTION OF THE INVENTION

Figure 1:
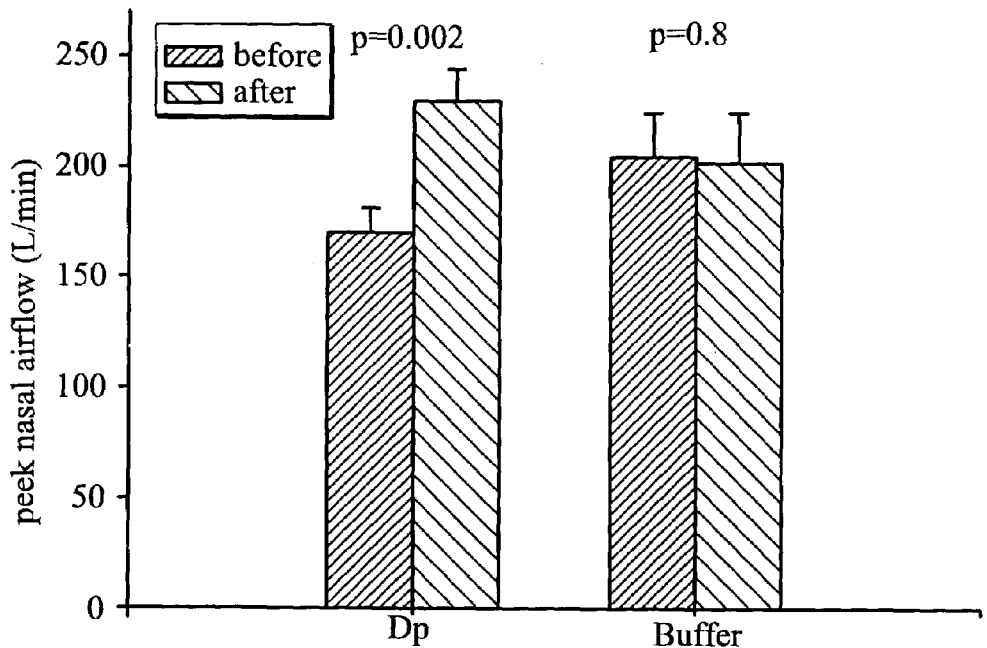
FIG. 1 is a diagram showing the effect of LNIT on peak nasal airflow. X axis represents the example (Dp) and control (buffer) groups, and Y axis represents the percentage of nasal airflow after provocation.

Previous study shows that nasal provocation tests with allergen disc paper can cause immediate nasal allergic reaction with trivial lower airway spasm or lower airway hyperresponsivity (Tsai Jaw-Ji, et al. Int Arch Allergy Immunol (1995) 106: 286–290). LNIT with a steady dosage of allergen has also been reported to have clinical efficacy and tolerability for AR (Bertoni M, et al. Ann Allergy Asthma Immunol (1999) 82:47–51). These reports indicate allergen disc paper with predefined dosage can be carried out for LNIT.

In order to avoid the potential risk of a systemic reaction, which may be caused by incorrect administration of allergen extract, allergen nasal or skin strips are used for LNIT. The present invention features a nasal or skin strip for treating or diagnosing allergen-induced airway inflammation in an individual. The nasal or skin strip comprises a substrate, and a mixture of an allergen and a pharmaceutically acceptable carrier on the substrate.

The present invention also features a method for diagnosing or treating allergen-induced airway inflammation. The method comprises applying a nasal or skin strip containing a mixture of an allergen and a pharmaceutically acceptable carrier to an individual having allergen-induced airway inflammation. For the purposes of diagnosis or treatment, the responsiveness of the individual, for example, release of symptoms, can be measured or monitored.

The "allergen-induced airway inflammation" used herein comprises, but is not limited to, allergic rhinitis, allergic conjunctivitis, or allergic bronchial asthma.

The "allergen" used herein comprises dust mite extract, pollen extract, mold extract, animal dander, cockroach extract, food allergen, recombinant allergen peptide or a combination thereof. The skin or nasal strip further comprises an immunomodulatory adjuvant. The "immunomodulatory adjuvant" used herein comprises fungal immunomodulatory protein (FIP) isolated from *Flammalina velutipes*, immunostimulatory sequence CpG (CpG oligodeoxynucleotides) or mycobacterium-Bacillus Calmette Guerin (BCG).

In one embodiment, the allergen extract is in a dosage of 0.01~10 $\mu$g, preferably 0.01~1 $\mu$g; the FIP is in a dosage of 0.01~10 $\mu$g, preferably 0.5 $\mu$g.

The preparation of the nasal or skin strip is described in the subsequent Materials and Methods section. In general, the allergen extract is in a concentration of 1~1000 $\mu$g/ml, preferably 1~ $\mu$g/ml; the FIP is in a concentration of 1~1000 $\mu$g/ml, preferably 250 $\mu$g/ml.

The "substrate" of the nasal or skin strip used herein includes nitrocellulose (NC), polyvinylidene fluoride (PVDF), nylon, filter papers, fabric, cloth, polyethylene, polypropylene, composite fibers, flexible medical grade materials, or a combination of above mentioned materials.

The "pharmaceutically acceptable carrier" used herein includes, but is not limited to, detergent, lipid solvent, glycerol, PBS, normal saline, water, petrolatum, or vaseline. The detergent includes lecithin or alpha hydroxyl acid, and the lipid solvent includes alcohol or mint. The glycerol is used in a concentration of 50% or more.

Without intending to limit in any manner, the present invention will be further illustrated by the following examples.

EXAMPLE

Materials and Methods

Subjects

Twenty-four subjects (10 females and 14 males) between 7 and 26 years of age (mean age 12 years) were chosen for the study. All patients had perennial rhinitis with typical histories of allergic rhinitis, i.e. house dust exposure could cause nasal symptoms including rhinorrhea, nasal stuffiness and sneezing. Six patients had histories of asthma symptoms after respiratory tract infection. All subjects had positive skin prick tests to Dp with the reaction size (wheal and flare) larger than the buffer control. At the time of study, all patients were free of asthma symptoms and required no oral medication and no local nasal spray for nasal symptom control except inhalation of $\beta$2-sympathetic agents for asthma symptom control. None had experienced allergy immunotherapy in the past. All subjects gave statements of informed consent and were recruited from the Allergy Clinic of the Cathay General Hospital, Taipei.

Nasal Provocation

Nasal challenge was performed as previously described (Tsai Jaw-Ji, et al. Int Arch Allergy Immunol (1995) 106: 286–290). The Dp extract (Pharmacia, Allergon A B, Engelholm, Sweden) was prepared at concentrations ranging from 1 to 10 $\mu$g/ml. Conventional short-acting antihistamines were withheld for at least 3 days before nasal challenge testing. A paper strip method was developed for nasal provocation. The provoking allergen extract, at different doses (1, 2, 5, 10 $\mu$g/ml), was contained in a strip paper (4 cm×0.5 cm) (Whatman filter paper No. 3; Whatman Ltd., UK), and 10 $\mu$l of liquid allergen at different concentrations was absorbed by each filter paper immediately before use. Strip paper was then placed onto the surface of the inferior turbinate. After provocation, most patients developed nasal symptoms with sneezing, nasal blockage and hypersection. Only those patients who developed the above symptoms were considered to have a positive response and were recruited for this study. The peak expiratory nasal airflow was measured to determine the degree of nasal obstruction using peak flow meter (Vitalograph Ltd, Buckingham, UK) before and after provocation. The percentage of peak nasal airflow after provocation was used to assess the airway hypersensitivity to Dp.

Program of LNIT

The LNIT was carried out during the period from September 1 to Dec. 1, 2001 according to a schedule based on subcutaneous injection every week. LNIT was performed at the Allergy Clinic Cathay General Hospital-Taipei. The nasal strip was applied to the same nostril each time by the same otolaryngologist for a total number of 12 administrations. The group of patients treated with Dp allergen extract received a steady dosage of 10 $\mu$l/strip in a concentration of 10 $\mu$g/ml. Such dose was chosen on the basis of the clinical evaluation of the nasal provocation carried out at the time of enrollment and was found to be the highest tolerated by all the patients.

Experimental Design

Patients were randomly divided into two groups. The treated group (10 patients) received Dp allergen strips, while the control group (14 patients) received the buffer saline. During the study, the serum level of Dp specific IgE was measured using Pharmacia CAP system (Kabi Pharmacia, Uppsala, Sweden). The peak expiratory nasal airflow was measured to determine the degree of nasal obstruction using peak flow meter (Vitalography Ltd) each time before therapy. All patients were kept a daily report of allergic symptoms including sneezing in the morning, rhinorrhea, nasal stuffiness and itchy nose during the whole course. The daily symptom score was 3 for severe, 2 for moderate, 1 for mild and 0 for no symptoms.

Statistical Analysis

The results were analyzed by paired Student's t test to compare the nasal symptoms, airway hypersensitivity, and peak nasal airflow before and after Dp LNIT in the same individuals. Non-paired Student's t test was used to analyze the differences between different groups of AR.

Results

Table 1 shows the general characteristics of the study population. As table 1 shows, both groups of patients were matched at baseline. There were no statistically significant variations between the IgE values of these two groups. Four patients, two for each group, withdrew from the study because of flu attack and poor response to therapy. There were no systemic reaction such as asthma and urticaria during treatment. Only mild sneezing and rhinorrhea occurred during the first 15 minutes after the strip application; however, this did not interfere with the LNIT.

TABLE 1

General characteristics of Study Populations

|  | Dp | Buffer | P value |
| --- | --- | --- | --- |
| Mean age(yr) ± SD | 11.8 (±3.34) | 12.9 (±4.49) | ns |
| Sex (M/F) | 8 (3/5) | 12 (8/4) | — |
| Pre-hyposensitizationIgE | 55.9 ± 26.0 | 70.6 ± 11.0 | 0.62 | ns: non-significant

Peak Expiratory Nasal Airflow Before and After LNIT

Peak expiratory nasal airflow was measured before and after LNIT. Results are shown in FIG. 1. Data is represented as the mean±SEM of 8 subjects treated with Dp allergen strips and 12 subjects treated with buffer saline control. The results show that there is a significant improvement in the group of patients who received Dp allergen LNIT. In this group, the peak nasal airflow is 169.4±11.2 l/min vs 228.8±14.5 l/min before and after LNIT (p=0.002). While in the group of buffer control, the peak nasal airflow is 194.6±17.4 l/min and 200.8±20.1 l/min before and after LNIT (p=0.70).

Nasal Airway Hypersensitivity to Dp Before and After LNIT

Figure 2:
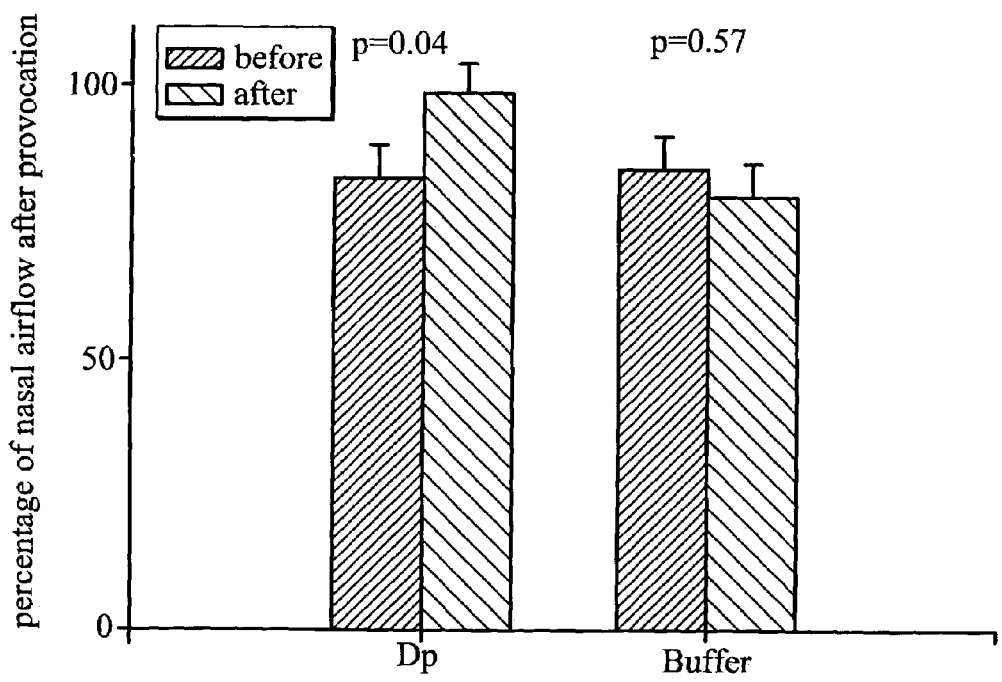
FIG. 2 is a diagram showing the effect of LNIT on nasal airway hypersensitivity. X axis represents the example (Dp) and control (buffer) groups, and Y axis represents peak nasal airflow (L/min).

Nasal provocation test was performed before and after LNIT. Nasal airflow was measured at 15 minutes after allergen nasal strip (10 µg/ml, 10 µl) application. Nasal airway hypersensitivity to Dp was determined as percentage of peak nasal airflow after Dp allergen strip challenge. Data were represented as mean±SEM of 8 subjects treated with Dp allergen strips and 5 subjects with buffer saline control. The results shown in FIG. 2 indicate that there is a statistically significant improvement in nasal airway hypersensitivity to Dp in the groups of patients receiving Dp allergen strip LNIT. When patients received buffer strip LNIT, the airway hypersensitivity to Dp remained the same.

Total Weekly Symptom Score Before and After LNIT

The total weekly symptom score for each group before and after LNIT were compared. The results shown in table 2 indicate that there is improvement of sneezing and rhinorrhea in both groups of patients. However, the improvement did not reach a statistically significant level. The symptoms of nasal stuffiness and itchy nose remain similar in both groups after LNIT.

TABLE 2

Mean Weekly Symptom Score

|  | Dp | | Buffer | |
| --- | --- | --- | --- | --- |
|  | Before | After | Before | After |
| Sneezing | 14.0 ± 4.5 | 9.6 ± 4.9 | 10.0 ± 4.2 | 4.3 ± 2.9 |
| Nasal stuffiness | 12.8 ± 6.6 | 16.4 ± 8.1 | 7.2 ± 5.8 | 12.6 ± 3.0 |
| Runningnose | 29.0 ± 9.2 | 15.4 ± 8.3 | 13.4 ± 5.8 | 7.5 ± 4.2 |
| Itchy nose | 16.3 ± 9.6 | 17.6 ± 5.2 | 7.0 ± 3.3 | 11.0 ± 4.6 |

Discussion

In the example, the clinical efficacy, safety and tolerability of Dp nasal strips on Dp allergic AR patients were evaluated. In addition to avoiding the incorrect administration of allergen extract into the lung, the allergen nasal strips were able to cause nasal allergic reaction in all patients. Moreover, the reaction was tolerable and could diminish the nasal airway hypersensitivity after LNIT with Dp nasal strips.

The major risk of allergen immunotherapy is anaphylaxis (Cohn J R, et al. J Allergy Clin Immunol (1993) 91:734–7; Committee on the Safety of Medicine. CSM update. Desensitizing vaccines. BMJ (1986) 293:948; Greenberg MA, et al. J Allergy Clin Immunol (1986) 77:865–70; Lockey R F, et al. J Allergy Clin Immunol (1987) 79:660–77). Asthma appears to be a significant risk factor for systemic reaction (Greenberg M A, et al. J Allergy Clin Immunol (1986) 77:865–70; Lockey R F, et al. J Allergy Clin Immunol (1987) 79:660–77). Although peak nasal airflow decreased in all patients following Dp nasal strip application, no systemic reaction or asthma was noted in this example. These results were in agreement with the previous report that nasal provocation with limited allergen using disc paper did not cause airway spasm or airway hypersensitivity to methacholine (Tsai Jaw-Ji, et al. Int Arch Allergy Immunol (1995) 106:286–290). Despite no systemic reaction in the report, it has been reported that systemic reaction can be caused by LNIT (Giannarin L, et al. Clin Exp Allergy (1998) 28:404–412). This discrepancy may be due to the different methods used for allergen application.

The examination of symptoms in subjects before and after LNIT shows that the symptoms of sneezing and rhinorrhea were slightly improved, but not with any statistical significance after LNIT with Dp nasal strips. Similar results occurred in the control group of subjects treated with buffer control. These findings were in disagreement with previous published results (Georgitis J W, et al. J Allergy Clin Immunol (1983) 71:71–6; Georgitis J W, et al. J Allergy Clin Immunol (1984) 74:694–700), wherein subjects treated with LNIT using aqueous allergoid grass pollen extract for 10 weeks showed improvement of nasal symptoms. These discrepancies may be due to different allergen extracts and patient selection.

Although it has been reported that LNIT can cause a reduction in nasal challenge test sensitivity, there was no appreciable change in the serum levels of allergen-specific IgE or IgG (Passalacqua G, et al. Am J Respir Crit Care Med (1995) 152:461–6; Giannarin L, et al. Clin Exp Allergy (1998) 28:404–412). Similar results are found in the example, wherein the nasal airway hypersensitivity to Dp was diminished after LNIT with Dp nasal strips. However, no statistically significant variance in Dp specific IgE before and after LNIT was found (data not shown). The decrease of allergen-specific T-cell response and the induction of T-cell tolerance by LNIT has been suggested to explain why LNIT is clinically effective in allergic patients with rhinitis (Giannarin L, et al. Clin Exp Allergy (1998) 28:404–412). Further studies are needed to clarify the working mechanisms linking with nasal airway hypersensitivity and the LNIT with allergen nasal strips.

In conclusion, the example suggests that LNIT with allergen nasal strips is safe and efficacious to improve nasal airway hypersensitivity to allergen, and may provide a good alternative for the treatment of allergic patients with rhinitis and asthma.

While the invention has been particularly shown and described with the reference to the preferred embodiments thereof, it will be understood by those skilled in the art that various changes in form and details may be made without departing from the spirit and scope of the invention.

What is claimed is:

1. A method for treating allergen-induced airway inflammation, comprising the step of:
    applying a nasal strip comprising a mixture of an allergen and a pharmaceutically acceptable carrier to the nostril of an individual having allergen-induced airway inflammation for local nasal immunotherapy.

2. The method as claimed in claim 1, wherein the allergen-induced airway inflammation comprises allergic rhinitis, allergic conjunctivitis or allergic bronchial asthma.

3. The method as claimed in claim 1, wherein the allergen comprises dust mite extract, pollen extract, mold extract, animal dander, cockroach extract, food allergen, recombinant allergen peptide, or a combination thereof.

4. The method as claimed in claim 1, wherein the nasal strip further comprises an immunomodulatory adjuvant.

5. The method as claimed in claim 4, wherein the immunomodulatory adjuvant comprises fungal immunomodulatory protein (FIP) isolated from *Flammalina velutipes*, immunostimulatory sequence CpG (CpG oligodeoxynucleotides), or *mycobacterium-Bacillus* Calmette Guerin (BCG).

6. The method as claimed in claim 1, wherein the pharmaceutically acceptable carrier is detergent, lipid solvent, glycerol, PBS, normal saline, water, petrolatum, or vaseline.

7. The method as claimed in claim 6, wherein the lipid solvent is alcohol or mint.

8. The method as claimed in claim 1, wherein the nasal or skin strip is nitrocellulose (NC), polyvinylidene fluoride (PVDF), nylon, filter paper, fabric, cloth, polyethylene, polypropylene, composite fibers, flexible medical grade materials, or a combination thereof.

9. The method as claimed in claim 3, wherein the allergen is in a dosage of 0.01~10 $\mu$g.

10. The method as claimed in claim 7, wherein the allergen is in a dosage of 0.01~1 $\mu$g.

* * * * *